United States Patent
Collica et al.

[11] 4,060,073
[45] Nov. 29, 1977

[54] SYRINGE SHIELD

[75] Inventors: Carl Collica, New Rochelle; Leonard Epifano, Rye; Ralph Farella, Scarsdale, all of N.Y.

[73] Assignee: Medi-Ray, Inc., Tuckahoe, N.Y.

[21] Appl. No.: 668,532

[22] Filed: Mar. 19, 1976

[51] Int. Cl.² .............................................. A61B 6/00
[52] U.S. Cl. ................................... 128/1.1; 128/2 A; 250/506
[58] Field of Search ............ 128/1.1, 2 A, 215, 218 P; 250/506

[56] References Cited
U.S. PATENT DOCUMENTS

| | | | |
|---|---|---|---|
| 3,596,659 | 8/1971 | Glasser | 128/215 |
| 3,814,941 | 6/1974 | Czaplinski | 128/1.1 X |
| 3,820,541 | 6/1974 | Langan | 128/215 |
| 3,973,554 | 8/1976 | Tipton | 128/1.1 |

Primary Examiner—John D. Yasko
Attorney, Agent, or Firm—Martin Novack

[57] ABSTRACT

A syringe shield having an inner generally cylindrical shell formed of plastic material. The shell has an elongated slot extending longitudinally therein and is open-ended at its rear end and narrows radially inward at its front end to form a tapered portion. A generally cylindrical body formed of radiation-shielding material is proportioned such that its inner surface conforms generally to the outer surface of the inner shell. The body has an elongated slot therein which is aligned with the slot in the inner shell. An outer shell, formed of plastic material, conforms to the shape of the outer surface of the body and has an elongated slot aligned with the slots in the inner shell in the body. An elongated optically transparent radiation shielding member is proportioned to fit in the elongated slot in the body. In the preferred embodiment of the invention the inner shell has a plurality of flexible plastic protrusions on the inner surface thereof. In this embodiment, the body tapers radially toward its axis at the front end thereof and a plastic ring-shaped collar joins the front edges of the inner and outer shells.

15 Claims, 4 Drawing Figures

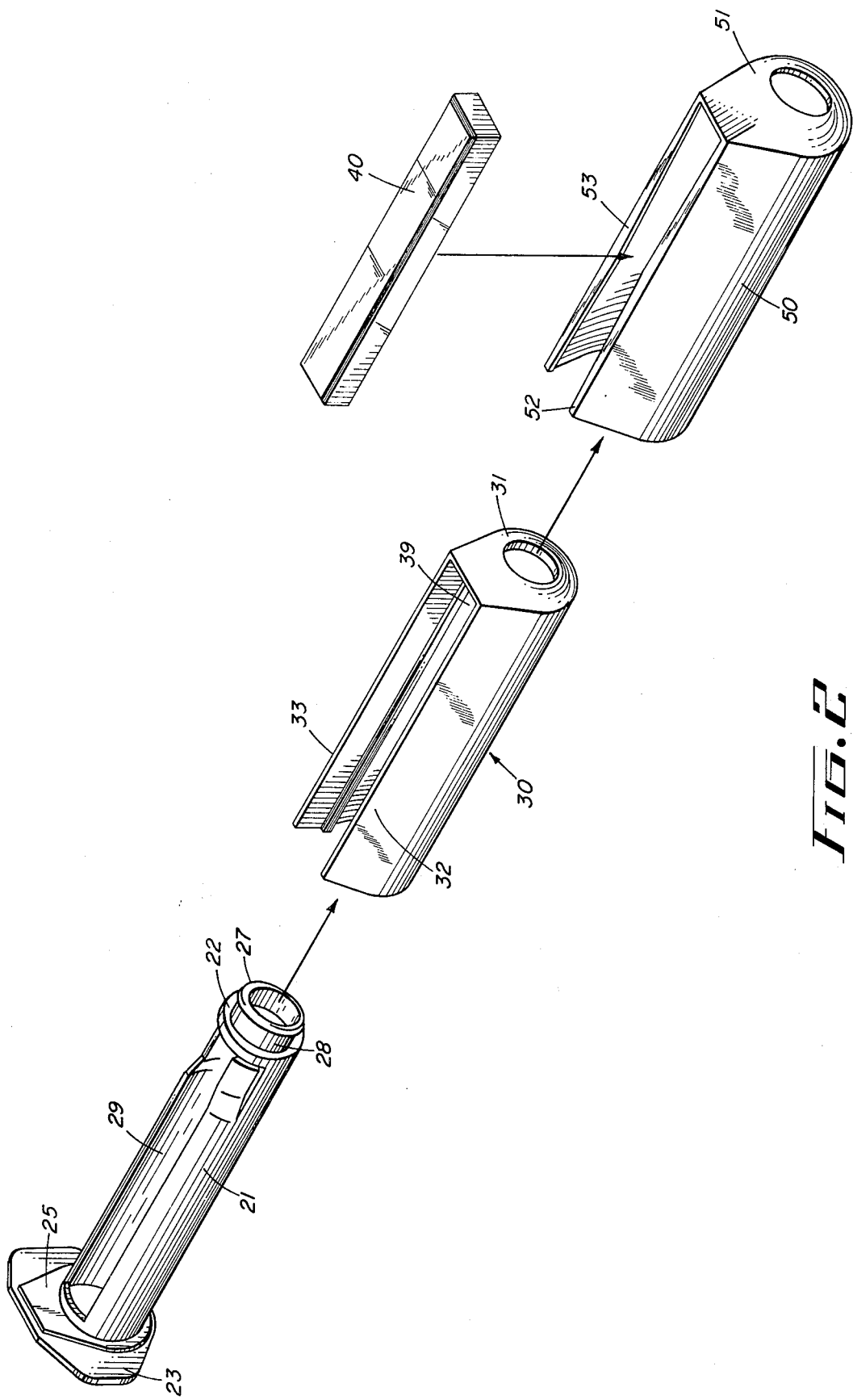

SYRINGE SHIELD

BACKGROUND OF THE INVENTION

This invention relates to the field of shielding radioactive materials and, more particularly, to an improved syringe shield.

The subject matter of this application relates to subject matter disclosed in the copending application Ser. No. 668,531 entitled "Shielded Syringe" filed of even date herewith and assigned to the same assignee as the present invention.

For various types of diagnostic testing it is necessary to inject radioactive materials into a patient. It is well recognized that technicians who handle these materials need protection against the perils of cumulative ionizing radiation exposure, so provision is commonly made for shielding the materials until such time as they are injected into the patient. Toward this end, various types of syringe shields have been developed. The typical prior art syringe shield includes a lead cylinder that fits over a syringe, the lead body having a window of leaded glass which allows the operator to see the scale on the syringe housed in the lead cylinder.

There are a number of disadvantages to presently available syringe shield designs. Some available units have a simple cylindrical casing which does not provide adequate shielding frontwardly or rearwardly of the syringe length. A further problem is that there is no standardization of syringe sizes, and even syringes having the same volume often have different physical dimensions. For example, a 10 cc syringe may have various possible diameters depending on the particular manufacturer. Thus, special provision is generally made to fit a syringe shield to the different possible syringe sizes. For example, in one prior art design the syringe shield is provided with a "set screw" which adjustably protrudes into the syringe shield's bore and engages the syringe so that it cannot move around within the syringe shield. The use of this technique involves some inconvenience and can occasionally cause breakage of the syringe.

The presence of a heavy shielding body, typically lead, is also problematic from the standpoint of unpleasantness of use. An unfinished lead exterior tends to become dirty and contaminated and is unsuitable for hospital conditions, whereas provisions for special finishing or plating may involve expense or introduction of unnecessarily cumbersome structures.

It is an object of this invention to provide a syringe shield which is responsive to the above recited problems of the prior art, while still being economical to manufacture and convenient to use.

SUMMARY OF THE INVENTION

The present invention is directed to a syringe shield having an inner generally cylindrical shell formed of plastic material. The shell has an elongated slot extending longitudinally therein and is open-ended at its rear end and narrows radially inward at its front end to form a tapered portion. A generally cylindrical body formed of radiation-shielding material is proportioned such that its inner surface conforms generally to the outer surface of the inner shell. The body has an elongated slot therein which is aligned with the slot in the inner shell. An outer shell, formed of plastic material, conforms to the shape of the outer surface of the body and has an elongated slot aligned with the slots in the inner shell in the body. An elongated optically transparent radiation shielding member is proportioned to fit in the elongated slot in the body.

In the preferred embodiment of the invention the inner shell has a plurality of flexible plastic protrusions on the inner surface thereof. In this embodiment, the body tapers radially toward its axis at the front end thereof and a ring-shaped collar, which may be an extension of the inner shell, joins the inner and outer shells at their front ends. The construction of the preferred embodiment requires only four parts and inexpensively achieves the objectives as set forth.

Further features and advantages of the invention will become more readily apparent from the following detailed description when taken in conjunction with the accompanying drawings.

BRIEF DESCRIPTION OF THE DRAWINGS

FIG. 2 is an exploded view of the syringe shield of FIG. 1.

DESCRIPTION OF THE PREFERRED EMBODIMENT

Figure 1:
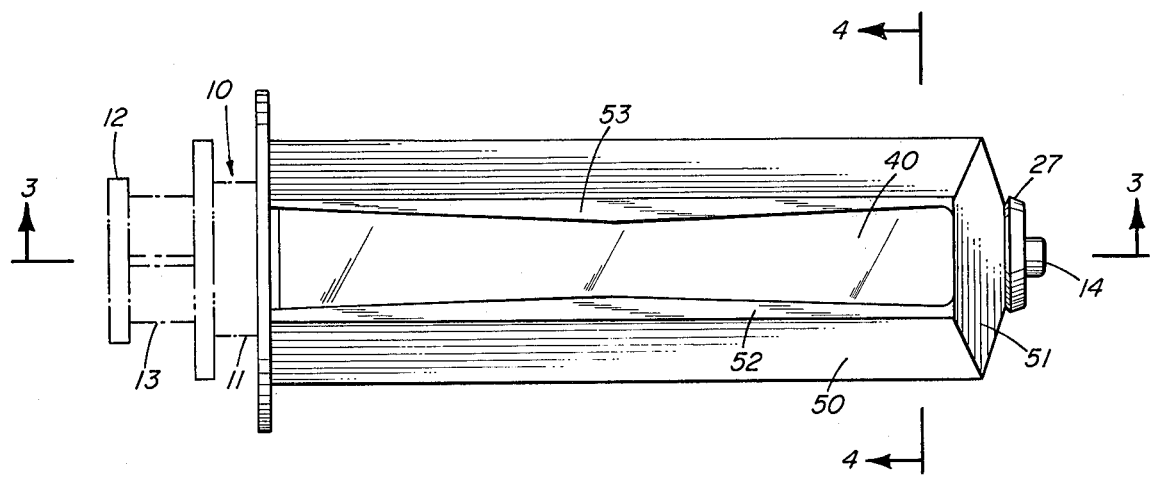
FIG. 1 is an elevational prospective view showing a syringe covered by a syringe shield in accordance with an embodiment of the invention.
Figure 3:
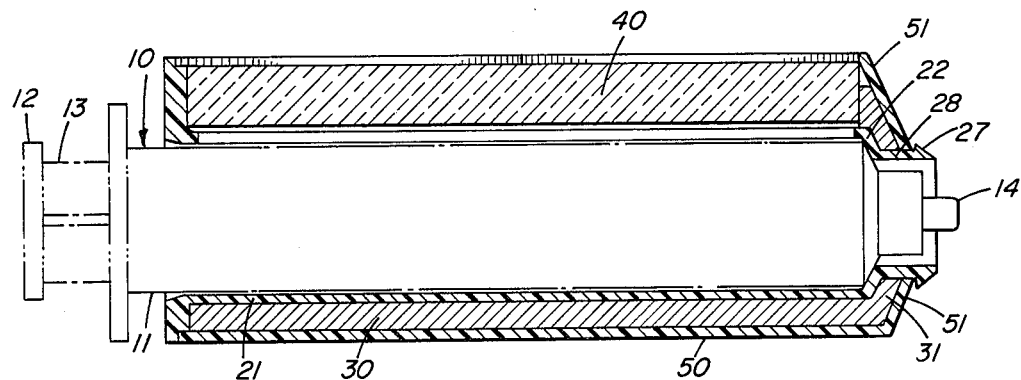
FIG. 3 is a cross-sectional view as taken through the section defined by arrows 3—3 of FIG. 1.
Figure 4:
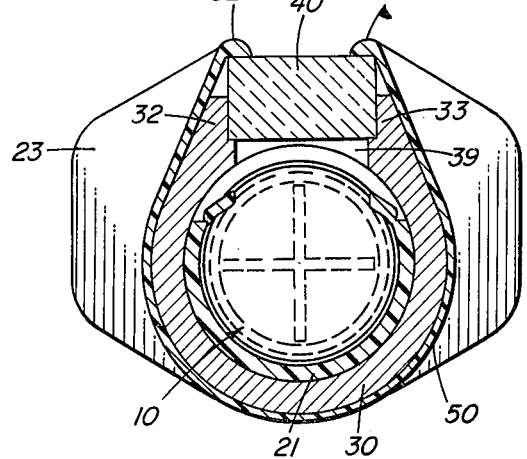
FIG. 4 is a cross-sectional view as taken through the section defined by arrows 4—4 of FIG. 1.

Referring to the drawings, there is shown a syringe 10 covered by a syringe shield 20 in accordance with an embodiment of the invention. The syringe 10 may be of conventional design, such as a 10 cc disposable syringe having a plastic body 11, a rear flange 12, a plunger 13 and a tip 14.

The syringe shield 20 has an inner generally cylindrical shell 21 formed of rigid plastic having an elongated rectangular slot therein. The shell 21 is open-ended at its rear end where it has a flange 23 and it narrows radially inwardly at its front end at 22. An extension collar 28, of reduced diameter, has an outwardly-extending annular protrusion 27 at its front edge.

A generally cylindrical body 30 is formed of a high density radiation-shielding material, such as lead. The body 30, which is also open-ended at its rear end and tapers at its front end at 31, is proportioned such that its inner surface conforms generally to the outside surface of the inner shell 21. The body has an elongated slot 39 extending along one side thereof which is aligned with the slot in the inner shell 21. The surface containing the slot 39 is flat on top and a pair of panels 32 and 33, which can be formed integrally of the same radiation-shielding material such as lead, are spaced slightly from the parallel edges of the slot and extend outwardly from the flat surface.

An elongated optically transparent radiation shielding member 40 is of rectangular shape in the present embodiment. The member 40 may be formed of leaded glass and will typically have a thickness which is substantially greater than that of the body 30. Thus, the shielding provided by the leaded glass, which is generally a less dense material than lead, will be comparable to the shielding provided by body 30, due to the greater thickness of the leaded glass. The member 40 is proportioned to fit within the panels 32 and 33 of the body 30 such that the member 40 overlays the periphery of slot 31 in the body 30.

An outer shell 50 is also preferably formed of a rigid plastic material and conforms generally in shape to the outer surface of shielding body 30. The outer shell 50 tapers inwardly at the front thereof (at 51) to form a circular aperture, the periphery of which joins the collar 28 of inner shell 21 just behind the annular protrusion 27. The outer shell 50 has a slot 59 aligned with the slots 29 and 31 in the inner shell 21 and body 30, respectively. The parallel edges of the slot 59 are lipped at 52 and 53 to retain the member 40.

To assemble the device, the inner shell 21 is inserted into the body 30 from the rear thereof. The flange 23 has a wall member 25 which is formed on its inner surface and serves as a spacer between the rear edge of body 130 and the flange. The body and inner shell are then inserted into the open ended rear of the outer shell 50 and the front aperture of shell 50 snaps over the protrusion 27. The rear edge of shell 50 fits over the periphery of wall 25 and is secured to the flange 23 by any suitable means, such as an epoxy bond.

The inner shell 21 has a pair of flexible plastic fingers or protrusions 26 which extend slightly into its bore near the front thereof, as shown. The degree to which the protrusions decrease the inner diameter of the bore depends on the degree to which they are flexed outward by the inserted syringe. Thus, a limited range of syringe diameters can be employed without the need for special adjustment and without an undesirable looseness of the syringe within the shield.

The invention has been described with reference to a particular embodiment, but it will be understood that variations within the spirit and scope of the invention will occur to those skilled in the art. In our above-referenced copending application there is disclosed an outer shell which removably retains an optically transparent radiation-shielding member. It will be appreciated that the optically transparent radiation shielding member of the present invention can be rendered removably retainable in accordance with the techniques set forth in our copending application; such as to facilitate assaying radioactive material in the syringe.

We claim:

1. A syringe shield, comprising:
   an inner generally cylindrical shell formed of poastic material having an elongated slot extending longitudinally therein;
   a generally cylindrical lead body, said body being proportioned such that its inner surface conforms generally to the outer surface of said inner shell, said body having an elongated slot aligned with the slot in said inner shell;
   an outer shell formed of plastic material, said outer shell having an elongated slot aligned with the slots in said inner shell and said body; and
   an elongated optically transparent radiation shielding member proportioned to fit in the elongated slot in said body.

2. The syringe shield as defined by claim 1 wherein said inner shell, said body, and said outer shell each taper radially toward their axis at the front end thereof, and further comprising a ring-shaped collar joining the tapered portions of the inner and outer shells at said front ends.

3. The syringe shield as defined by claim 2 wherein said collar is a front extension of said inner shell.

4. The syringe shield as defined by claim 1 wherein said inner shell has a plurality of flexible plastic protrusions extending into its bore.

5. The syringe shield as defined by claim 2 wherein said inner shell has a plurality of flexible plastic protrusions extending into its bore.

6. The syringe shield as defined by claim 1 wherein said slots are generally rectangular and wherein said outer shell is lipped at its slot to retain said member.

7. The syringe shield as defined by claim 2 wherein said slots are generally rectangular and wherein said outer shell is lipped at its slot to retain said member.

8. The syringe shield as defined by claim 5 wherein said slots are generally rectangular and wherein said outer shell is lipped at its slot to retain said member.

9. A syringe shield, comprising:
   an inner generally cylindrical shell formed of plastic material having an elongated slot extending longitudinally therein;
   a generally cylindrical body of radiation-shielding material, said body being proportioned such that its inner surface conforms generally to the outer surface of said inner shell, said body having an elongated slot aligned with the slot in said inner shell;
   an outer shell formed of plastic material, said outer shell having an elongated slot aligned with the slots in said inner shell and said body, said inner shell, said body, and said outer shell each tapering radially toward their axis at the front end thereof;
   a ring-shaped collar joining the tapered portions of the inner and outer shells at said front ends; and
   an elongated optically transparent radiation shielding member proportioned to fit in the elongated slot in said body.

10. The syringe shield as defined by claim 9 wherein said collar is a front extension of said inner shell.

11. The syringe shield as defined by claim 9 wherein said inner shell has a plurality of flexible plastic protrusions extending into its bore.

12. The syringe shield as defined by claim 9 wherein said slots are generally rectangular and wherein said outer shell is lipped at its slot to retain said member.

13. The syringe shield as defined by claim 11 wherein said slots are generally rectangular and wherein said outer shell is lipped at its slot to retain said member.

14. A syringe shield, comprising:
   an inner generally cylindrical shell formed of plastic material having an elongated slot extending longitudinally therein, said inner shell having a plurality of flexible plastic protrusions into its bore;
   a generally cylindrical body of radiation-shielding material, said body being proportioned such that its inner surface conforms generally to the outer surface of said inner shell, said body having an elongated slot aligned with the slot in said inner shell;
   an outer shell formed of plastic material, said outer shell having an elongated slot aligned with the slots in said inner shell and said body; and
   an elongated optically transparent radiation shielding member proportioned to fit in the elongated slot in said body.

15. A syringe shield, comprising:
   an inner generally cylindrical shell formed of plastic material having an elongated generally rectangular slot extending longitudinally therein;
   a generally cylindrical body of radiation-shielding material, said body being proportioned such that its inner surface conforms generally to the outer surface of said inner shell, said body having an elongated generally rectangular slot aligned with the slot in said inner shell;

an outer shell formed of plastic material, said outer shell having an elongated generally rectangular slot aligned with the slots in said inner shell and said body; and an elongated optically transparent radiation shielding member proportioned to fit in the elongated slot in said body; said outer shell being lipped at its slot to retain said member.

* * * * *